(12) United States Patent
Morgan et al.

(10) Patent No.: US 10,337,159 B2
(45) Date of Patent: Jul. 2, 2019

(54) VIS-NIR EQUIPPED SOIL PENETROMETER

(71) Applicants: The Texas A&M University System, College Station, TX (US); Washington State University, Pullman, WA (US)

(72) Inventors: Cristine Morgan, College Station, TX (US); Yufeng Ge, College Station, TX (US); David Brown, Pullman, WA (US); Ross Bricklemyer, Pullman, WA (US)

(73) Assignees: The Texas A&M University System, College Station, TX (US); Washington State University, Pullman, WA (US)

( * ) Notice: Subject to any disclaimer, the term of this patent is extended or adjusted under 35 U.S.C. 154(b) by 0 days.

(21) Appl. No.: 15/631,470

(22) Filed: Jun. 23, 2017

(65) Prior Publication Data
US 2017/0370064 A1 Dec. 28, 2017

Related U.S. Application Data

(60) Provisional application No. 62/353,716, filed on Jun. 23, 2016.

(51) Int. Cl.
| | |
|---|---|
| E02D 1/02 | (2006.01) |
| G01J 3/02 | (2006.01) |
| G01J 3/10 | (2006.01) |
| G01N 21/01 | (2006.01) |
| G01N 33/24 | (2006.01) |
| G01N 21/85 | (2006.01) |

(52) U.S. Cl.
CPC ............ *E02D 1/027* (2013.01); *G01J 3/0208* (2013.01); *G01J 3/0272* (2013.01); *G01J 3/0291* (2013.01); *G01J 3/108* (2013.01); *G01N 21/01* (2013.01); *G01N 21/8507* (2013.01); *G01N 33/24* (2013.01); *G01N 33/246* (2013.01)

(58) Field of Classification Search
CPC ....... E02D 1/027; G01J 3/0208; G01J 3/0272; G01J 3/0291; G01J 3/108; G01N 21/01; G01N 33/246
See application file for complete search history.

(56) References Cited

U.S. PATENT DOCUMENTS

| | | | | |
|---|---|---|---|---|
| 5,739,536 | A | * 4/1998 | Bucholtz | G01J 3/02 250/253 |
| 2011/0106451 | A1 | * 5/2011 | Christy | G01N 21/359 702/5 |

OTHER PUBLICATIONS

Ben-Dor et al., "A novel method of classifying soil profiles in the field using optical means," Soil Science Society of America Journal, Jul.-Aug. 2008, pp. 1113-1123, vol. 72, No. 4.
(Continued)

*Primary Examiner* — Mark R Gaworecki
(74) *Attorney, Agent, or Firm* — Saliwanchik, Lloyd & Eisenschenk

(57) ABSTRACT

Soil penetrometers capable of measuring soil reflectance along the direction of insertion of the penetrometer are provided. The penetrometer can house an array of sensors, such as, for example, a Vis-NIR reflectance sensor, a load cell, a displacement sensor, and a moisture sensor. The reflectance data collected using the penetrometer can allow the interpretation and quantification of soil constituents and contaminants at high vertical resolution, such as 3 cm or more.

15 Claims, 15 Drawing Sheets

(56) References Cited

OTHER PUBLICATIONS

Bogrekci et al., "Effects of soil moisture content on absorbance spectra of sandy soils in sensing phosphorus concentrations using UV-VIS-NIR spectroscopy," Transactions of the ASABE, 2006, pp. 1175-1180, vol. 49, No. 4.
Bricklemyer et al., "On-the-go VisNIR: potential and limitations for mapping soil clay and organic carbon," Computers and Electronics in Agriculture, Jan. 2010, pp. 209-216, vol. 70.
Brown et al., "Global soil characterization with VNIR diffuse reflectance spectroscopy," Geoderma, Jun. 2006, pp. 273-290, vol. 132.
Chang et al., "Near-infrared reflectance spectroscopy-principal components regression analyses of soil properties," Soil Science Society of America Journal, Mar.-Apr. 2001, pp. 480-490, vol. 65.
Christy, "Real-time measurement of soil attributes using on-the-go near infrared reflectance spectroscopy," Computers and Electronics in Agriculture, Apr. 2008, pp. 10-19, vol. 61.
Gauch et al., "Model evaluation by comparison of model-based predictions and measured values," Agronomy Journal, Nov.-Dec. 2003, pp. 1442-1446, vol. 95.
Gomez et al., "Soil organic carbon prediction by hyperspectral remote sensing and field vis-NIR spectroscopy: an australian case study," Geoderma, Aug. 2008, pp. 403-411, vol. 146.
Idso et al., The dependence of bare soil albedo on soil water content, Journal of Applied Meteorology, Feb. 1975, pp. 109-113, vol. 14.
Kaleita et al., "Relationship between soil moisture content and soil surface reflectance," Transactions of the ASAE, 2005, pp. 1979-1986, vol. 48, No. 5.
Lobell et al., "Moisture effects on soil reflectance," Soil Science Society of America Journal, May-Jun. 2002, pp. 722-727, vol. 66.
Loeppert et al., "Carbonate and gypsum," Methods of Soil Analysis, Part 3: Chemical Methods, 1996, pp. 437-474.
Minasny et al., "Evaluating near infrared spectroscopy for field prediction of soil properties," Australian Journal of Soil Research, Nov. 2009, pp. 664-673, vol. 47.
Minasny et al., "Removing the effect of soil moisture from NIR diffuse reflectance spectra for the prediction of soil organic carbon," Geoderma, Nov. 2011, pp. 118-124, vol. 167-168.
Muller et al., "Modeling soil moisture-reflectance," Remote Sensing of Environment, May 2001, pp. 173-180, vol. 76, No. 2, Author version.
Roger et al., "EPO-PLS external parameter orthogonalisation of PLS application to temperature-independent measurement of sugar content of intact fruits," Chemometrics and Intelligent Laboratory Systems, Jun. 2003, pp. 191-204, vol. 66, No. 2, Author version.
Sankey et al., "Comparing local vs. global visible and near-infrared (VisNIR) diffuse reflectance spectroscopy (DRS) calibrations for the prediction of soil clay, organic C and inorganic C," Geoderma, Dec. 2008, pp. 149-158, vol. 148.
Shepherd et al., "Development of reflectance spectral libraries for characterization of soil properties," Soil Science Society of America Journal, May-Jun. 2002, pp. 988-998, vol. 66.
Sherrod et al., "Inorganic carbon analysis by modified pressure-calcimeter method," Soil Science Society of America Journal, Jan.-Feb. 2002, pp. 299-305, vol. 66.
Stenberg et al., "Visible and near infrared spectroscopy in soil science," Advances in Agronomy, 2010, pp. 163-215, vol. 107, Author version.
Sudduth et al., "Portable, near-infrared spectrophotometer for rapid soil analysis," Transactions of the ASAE, Jan.-Feb. 1993, pp. 185-193, vol. 36, No. 1.
Viscarra Rossel et al., "Visible, near infrared, mid infrared or combined diffuse reflectance spectroscopy for simultaneous assessment of various soil properties," Geoderma, Mar. 2006, pp. 59-75, vol. 131.
Viscarra Rossel et al., "In situ measurements of soil colour, mineral composition and clay content by vis-NIR spectroscopy," Geoderma, May 2009, pp. 253-266, vol. 150.
Zhu et al., "Characterizing surface soil water with field portable diffuse reflectance spectroscopy," Journal of Hydrology, Sep. 2010, pp. 133-140, vol. 391.
Waiser et al., "In situ characterization of soil clay content with visible near-infrared diffuse reflectance spectroscopy," Soil Science Society of America Journal, Mar. 2007, pp. 389-396, vol. 71, No. 2.
Gee et al., "Particle-size analysis," Methods of Soil Analysis: Part 4—Physical Methods, Jan. 2002, pp. 255-293.
Mouazen et al., "On-line measurement of some selected soil properties using a VIS-NIR sensor," Soil and Tillage Research, Mar. 2007, pp. 13-27, vol. 93.
Slaughter et al., "Sensing soil moisture using NIR spectroscopy," Applied Engineering in Agriculture, Mar. 2001, pp. 241-247, vol. 17, No. 2.
Ge et al., "VisNIR spectra of dried ground soils predict properties of soils scanned moist and intact," Geoderma, Jun. 2014, pp. 61-69, vol. 221-222.
Poggio et al., "Laboratory-based evaluation of optical performance for a new soil penetrometer visible and near-infrared (VisNIR) foreoptic," Computers and Electronics in Agriculture, Jun. 2015, pp. 12-20, vol. 115.
Nelson et al., "Total carbon, organic carbon, and organic matter," Methods of Soil Analysis: Part 3—Chemical Methods, Jan. 1996, pp. 961-1010.
Twomey et al., "Reflectance and albedo differences between wet and dry surfaces," Applied Optics, Feb. 1986, pp. 431-437, vol. 25, No. 3.
Morgan et al., "Simulated in situ characterization of soil organic and inorganic carbon with visible near-infrared diffuse reflectance spectroscopy," Geoderma, Jul. 2009, pp. 249-256, vol. 151.
Ackerson et al., "A Universal Transformation to Remove the Effect of Water Content from Vis NIR Spectra", Paper presented at: 2013 Soil Survey & Land Resources Workshop, 2014.
Ackerson et al., "Are VisNIR Orthotognal Projection Matrices Universal?", Poster presented at: Water, Food, Energy, and Innovation for a Sustainable World, ASA, CSSA, and SSSA Annual Meetings, 2013.

* cited by examiner

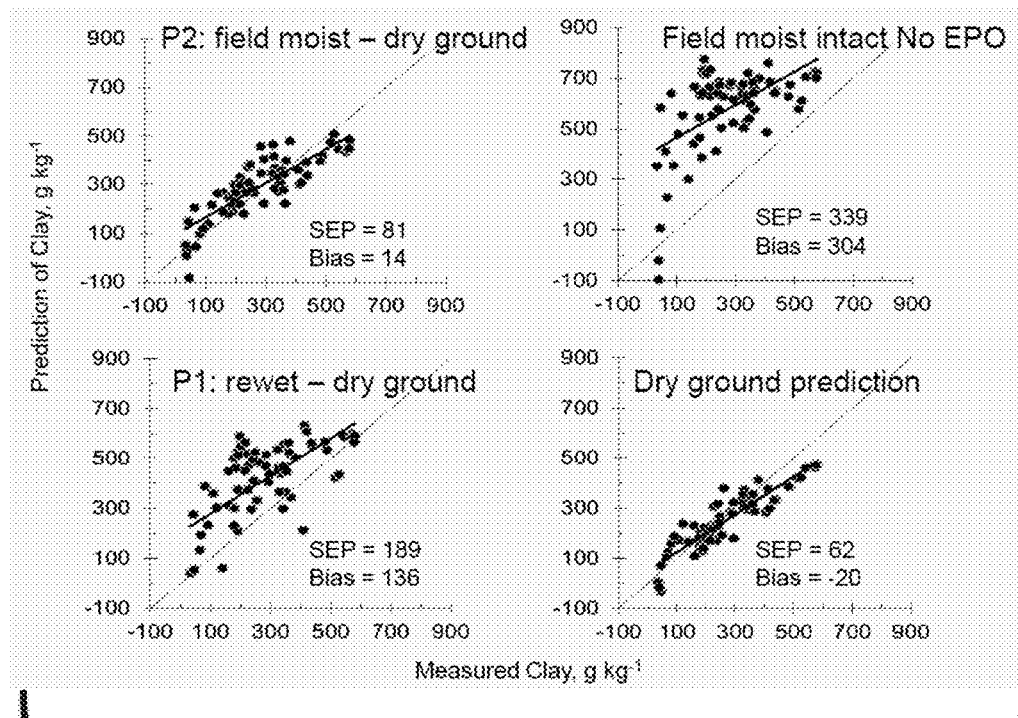
FIG. 11
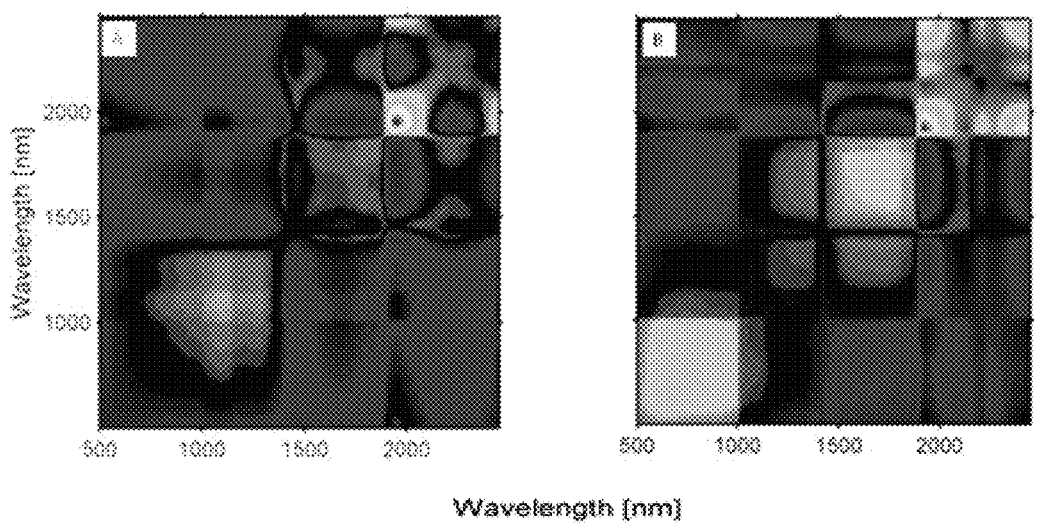
FIG. 12A                    FIG. 12B

VIS-NIR EQUIPPED SOIL PENETROMETER

CROSS-REFERENCE TO RELATED APPLICATION

The present application claims the benefit of U.S. Provisional Application Ser. No. 62/353,716, filed Jun. 23, 2016, which is incorporated herein by reference in its entirety, including any figures, tables, and drawings.

GOVERNMENT SUPPORT

The subject invention was made with government support under 68-7482-2-39 awarded by USDA Natural Resources Conservation Services (NRCS), USDA-NIFA Award No. 2011-67003-30341, and under DE-FC26-05NT42587 awarded by U.S. Department of Energy National Energy Technology Laboratory to Dr. David Joseph Brown et al. The government has certain rights in the invention.

BACKGROUND OF INVENTION

Visible and near infrared reflectance spectroscopy (Vis-NIR) is widely used as a rapid and cost-effective technique for quantitative analysis of many soil properties. However, existing Vis-NIR-based instruments for in situ characterization of soil have many limitations and face challenges when attempting to obtain high resolution spatial and temporal soil data intended for precision agriculture, soil survey and mapping, land resource management, and soil modeling.

BRIEF SUMMARY

The subject invention provides soil penetrometers capable of measuring soil reflectance in the direction of insertion of the penetrometer, as well as methods of fabricating and using the same. The penetrometer can house a sensor or an array of sensors, including, for example, one or more visible and near infrared reflectance spectroscopy Vis-NIR reflectance sensors, load cells, displacement sensors, and/or moisture sensors. The reflectance data collected using the penetrometer provided herein allow the interpretation and quantification of soil constituents and contaminants at higher vertical resolution (e.g., approximately 3 cm or more) than conventional penetrometers.

In an embodiment, a soil penetrometer can include an optical module enclosed in a housing (e.g., a tubular housing), which is connected to a tip (e.g., a conical tip) at one end and a connector (e.g., a tubular connector) at the opposite end. The connector (e.g., tubular connector) can be connected to an extension rod. The housing (e.g., tubular housing) can further include a transparent window, which can include or be made of, for example, sapphire. The optical module can include a mirror, a light-emitting device, and/or a fiber optic sensor, which can be fixed in the vicinity of, and at a pre-determined angle with respect to, the plane parallel to the transparent window.

In a further embodiment, the connector (e.g., tubular connector) can enclose one or more sensing devices. The connector can be connected to the housing at one end and detachably connected to the extension rod at the opposite end.

In yet a further embodiment, the extension rod can be detachably connected to another device or a combination of devices at the end opposite to the connector.

The soil penetrometer can be plugged into an existing Vis-NIR spectrometer that is capable of quantifying soil constituents. In some embodiments, the penetrometer with the spectrometer attached is field-portable.

Advantageously, the subject invention enhances the ability to collect in situ high resolution reflectance data for soil constituent interpretation and quantification and can be widely used by researchers in fields such as natural resource management, hydrologic modeling, soil mapping, and precision agriculture.

BRIEF DESCRIPTION OF THE DRAWINGS

FIG. 11 shows Vis-NIR predictions of clay content using dry-ground spectral libraries made on dry-ground soil. Using the same library, predictions were made on intact and moist soil with and without EPO, respectively.

FIG. 12A shows a P-matrix generated on soil from Texas.

FIG. 12B shows a P-matrix generated on soil from Australia.

DETAILED DISCLOSURE

The subject invention provides soil penetrometers capable of measuring soil reflectance in the direction of insertion of the penetrometer, as well as methods of fabricating and using the same. The penetrometer can house a sensor or an array of sensors, including, for example, one or more visible and near infrared reflectance spectroscopy Vis-NIR reflectance sensors, load cells, displacement sensors, and/or moisture sensors. The reflectance data collected using the penetrometer provided herein allow the interpretation and quantification of soil constituents and contaminants at higher vertical resolution (e.g., approximately 3 cm or more) than conventional penetrometers.

Figure 1:
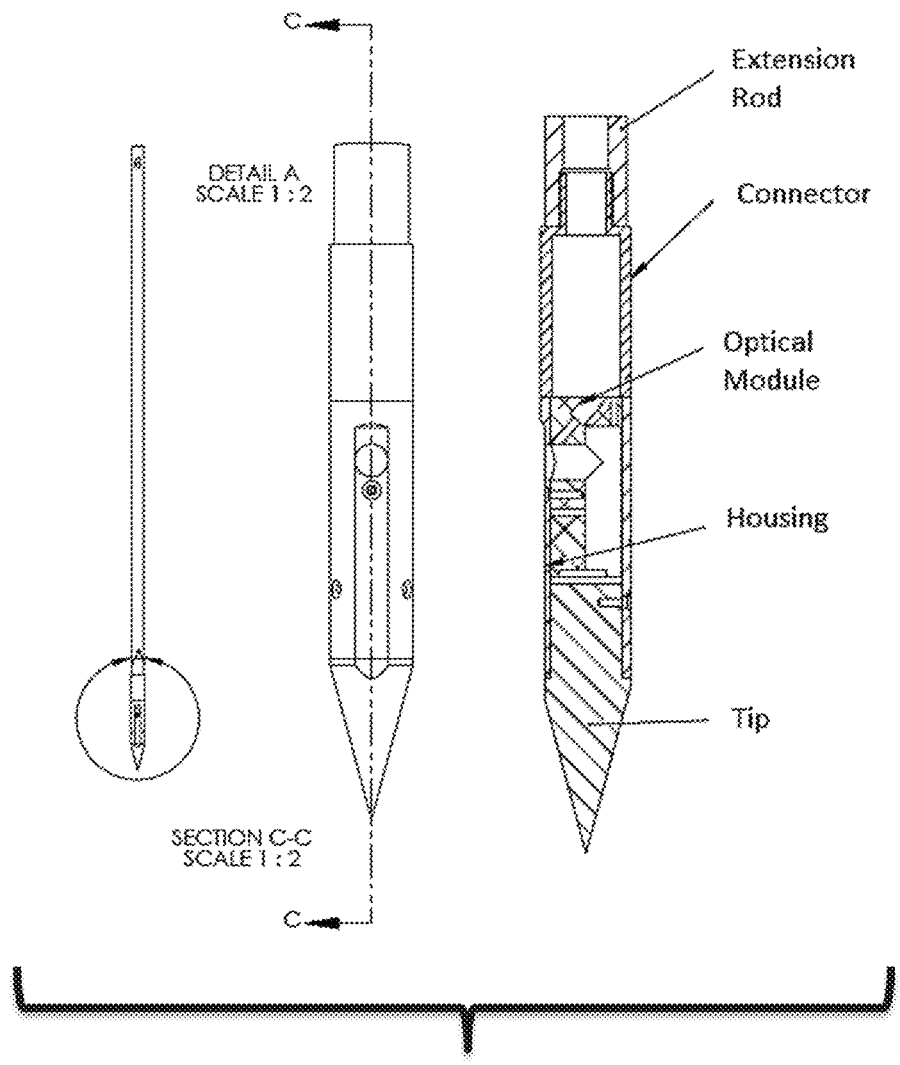
FIG. 1 shows a schematic view of a penetrometer according to an embodiment of the subject invention.
Figure 4:
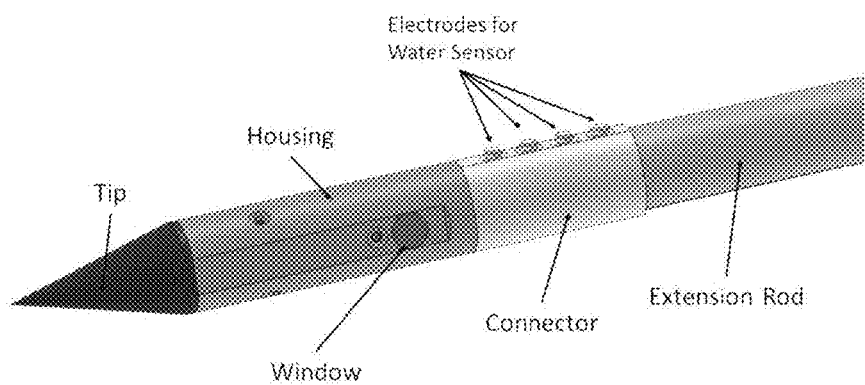
FIG. 4 shows a schematic view of an external portion of a penetrometer according to an embodiment of the subject invention.

In many embodiments, the soil penetrometer can include an optical module enclosed in a housing (e.g., a tubular housing), which is connected to a tip (e.g., a conical tip) at one end and a connector (e.g., a tubular connector) at the opposite end. The connector (e.g., tubular connector) can be further connected to an extension rod (as shown in FIGS. 1 and 4). The (tubular) housing can further include a transparent window, which can be a sapphire window, though embodiments are not limited thereto. The window can be designed to facilitate transmission of light between the optical module and the soil sample. The window (e.g., sapphire window) can measure approximately 0.5 inch in diameter and can be built into the wall of the (tubular) housing.

Figure 14:
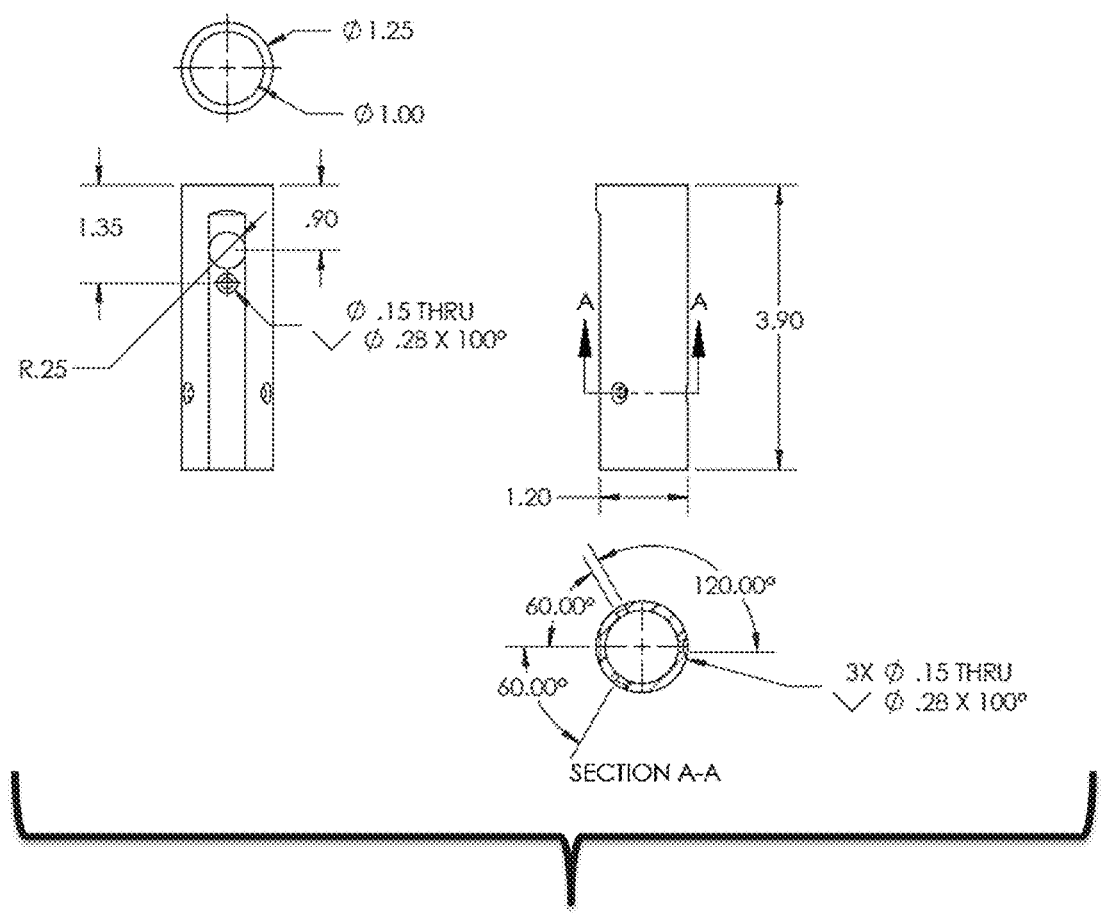
FIG. 14 shows a schematic view of a tubular housing of a penetrometer according to an embodiment of the subject invention.

In an embodiment, the outer diameter of a tubular housing can be approximately 1.25 inch, and the inner diameter can be approximately 1.0 inch (as shown in FIG. 14).

In a specific embodiment, the body of the (tubular) housing can include or be made from stainless steel.

Figure 2:
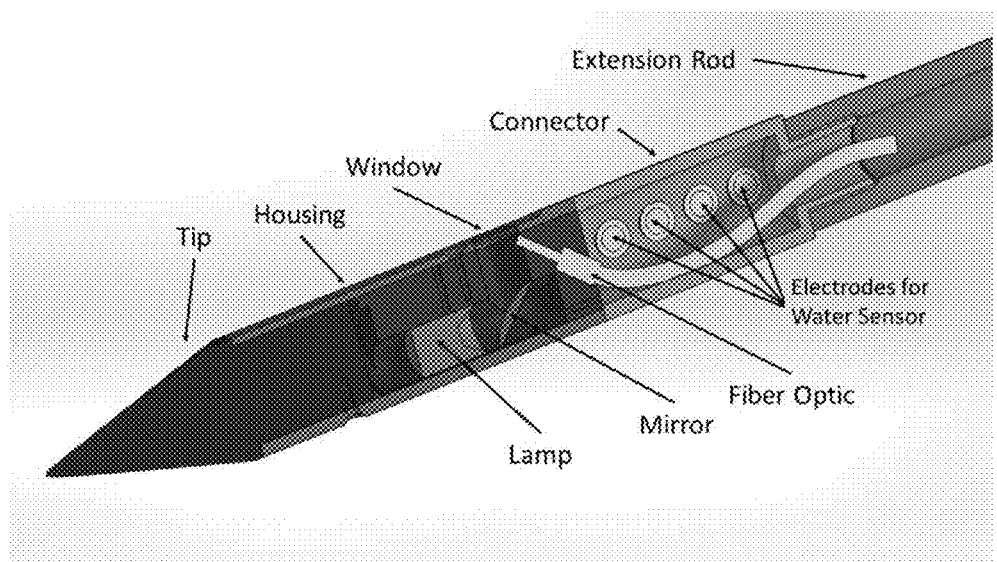
FIG. 2 shows a cross-sectional view of a penetrometer according to an embodiment of the subject invention having a moisture sensor enclosed in the connector.
Figure 15:
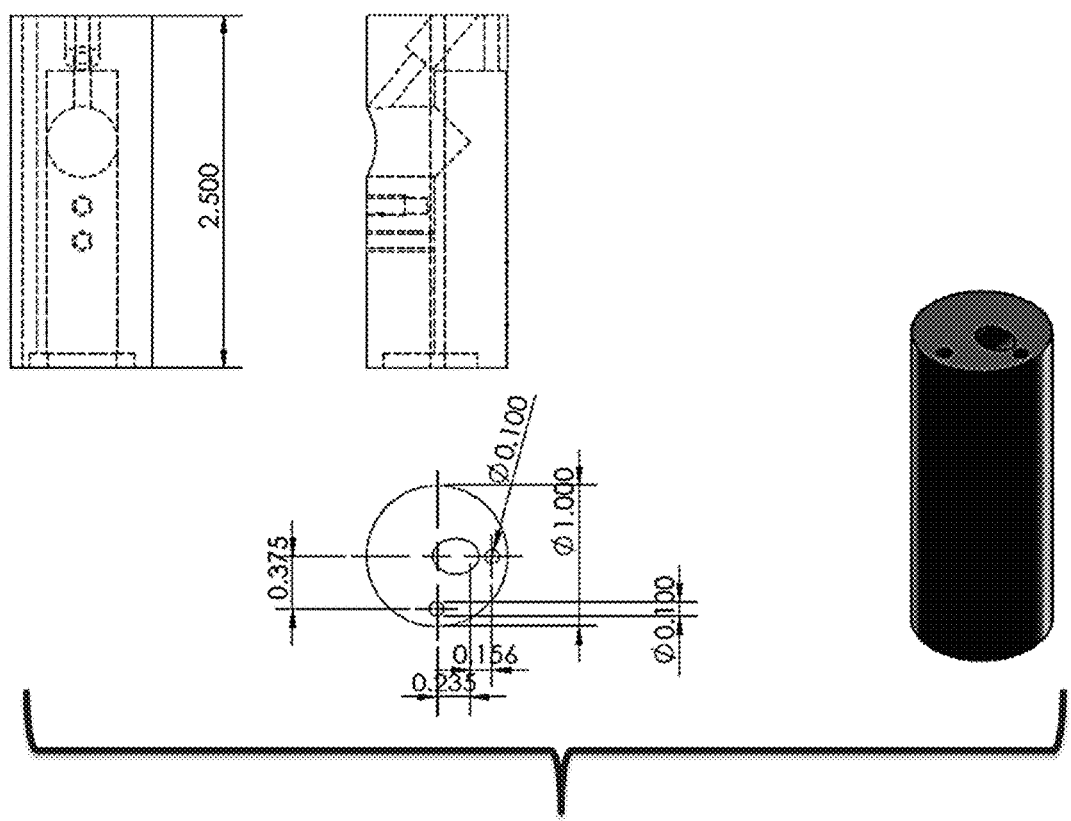
FIG. 15 shows a schematic view of an optical module unit of a penetrometer according to an embodiment of the subject invention.

In many embodiments, the optical module can include a mirror, a light-emitting device, and/or a fiber optic sensor, which can be fixed at a pre-determined angle with respect to the plane parallel to the transparent window (as shown in FIG. 2) (that is, the plane parallel to the flat surface of the window). In an embodiment, the angle between fiber optic sensor and the plane parallel to the transparent window is between about 40 degrees to about 55 degrees. In an embodiment, the optical module can be enclosed in a casing (e.g., an aluminum casing) having a diameter that measures approximately 1.0 inch (as shown in FIG. 15).

Figure 3:
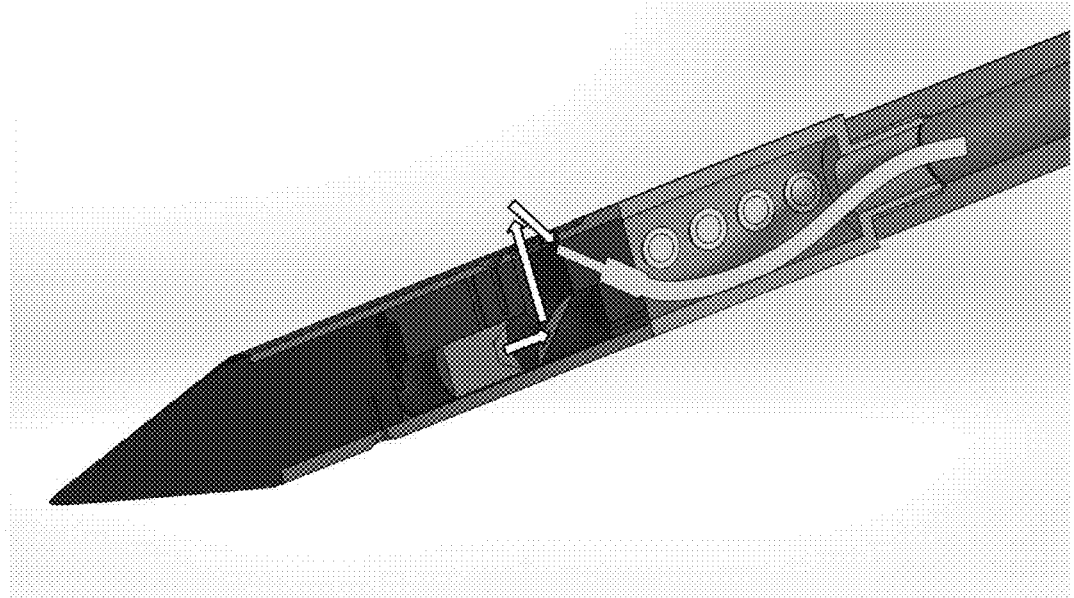
FIG. 3 shows a cross-sectional view of a penetrometer according to an embodiment of the subject invention, indicating the path of light within the optical module.

According to some embodiments of the subject invention, the mechanism of signal generation and detection by which the soil sample is analyzed can be described by the following process (FIG. 3). Light is first generated by the light-emitting device such as, for example, a lamp, a light-emitting diode (LED), or the like. The light is then reflected by the mirror and subsequently transmitted through the window (e.g., sapphire window). After the light interacts with the soil, the reflected signal is transmitted back through the window and subsequently detected by the fiber optic sensor. In a specific embodiment, the fiber optic sensor is connected to a Vis-NIR spectrometer of choice as well as any other additional devices and components needed to acquire spectral scans such as, for example, data logging and power supply equipment. In certain embodiments, the wiring between the fiber optic sensor and the spectrometer can be enclosed within the cavity of the penetrometer.

Artisans skilled in the pertinent field would appreciate that the geometric arrangement of the fiber optic sensor with respect to the plane parallel to the window (e.g., sapphire window) matches that of an industry-standard tool for collecting soil spectra under laboratory conditions. A non-limiting example of the tool is a mug lamp, such as the one manufactured by the Analytical Spectral Devices Inc. Advantageously, depending upon the specific spectrometer employed and the signal-to-noise ratio desired, different geometric arrangements of the optical module can be accommodated by embodiments of the penetrometer of the subject invention, making it customizable.

In many embodiments, the soil penetrometer can be plugged into an existing Vis-NIR spectrometer that is capable of quantifying soil constituents in the laboratory. In a specific embodiment, the spectrometer employed herein can collect soil reflectance data in a range of between approximately 350 nm and approximately 2500 nm.

In some embodiments, the penetrometer is equipped with a multi-sensor platform comprising devices for measuring one or more parameters including, but not limited to, time-domain reflectometry (TDR), penetration resistance, displacement, and load.

Figure 9:
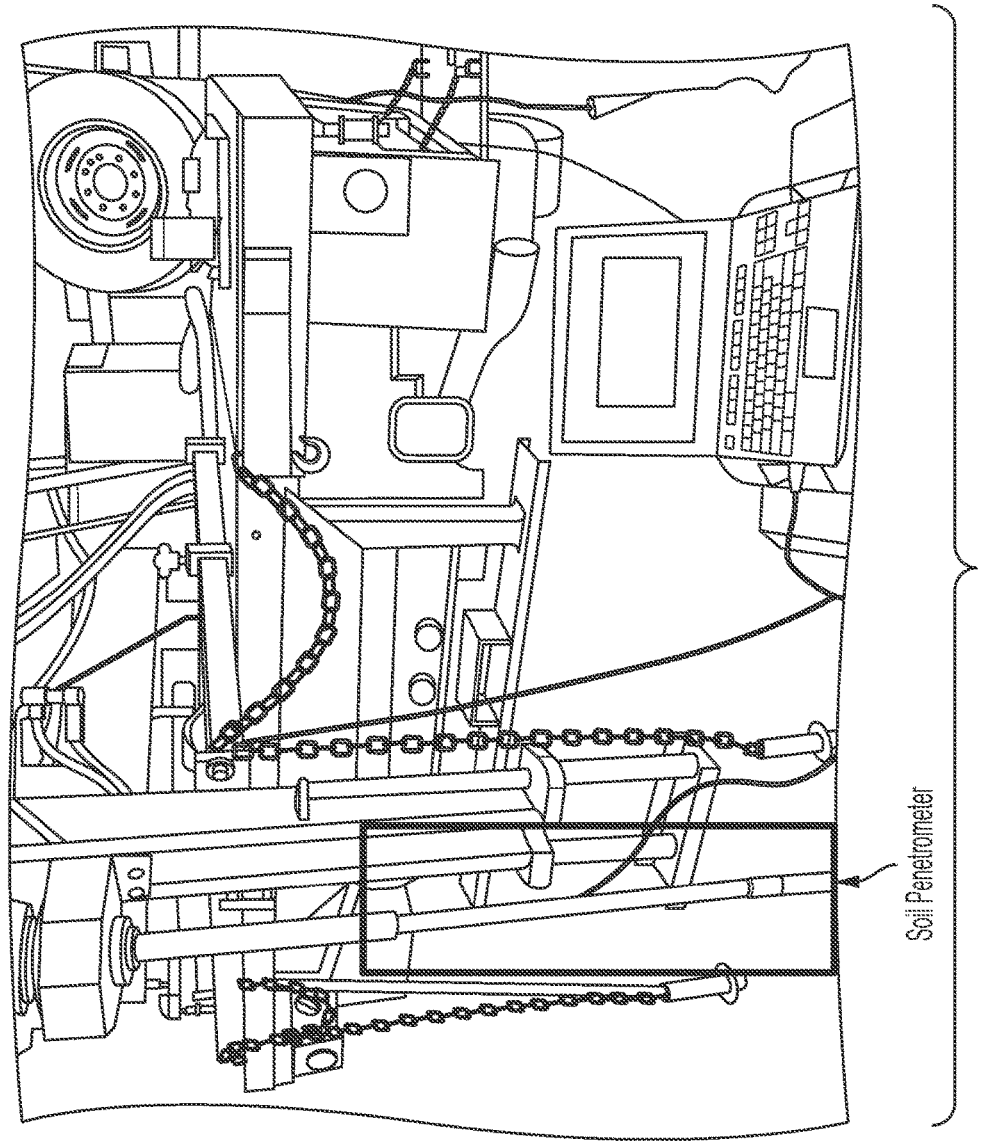
FIG. 9 shows a image of a penetrometer according to an embodiment of the subject invention connected to a Vis-NIR spectrometer and mounted on a soil probe truck during a field test.

In some embodiments, the penetrometer is made field-portable by being connected to devices including but not limited to trucks, all-terrain vehicles, and tractor-mounted hydraulic soil probes (FIG. 9).

Figure 16:
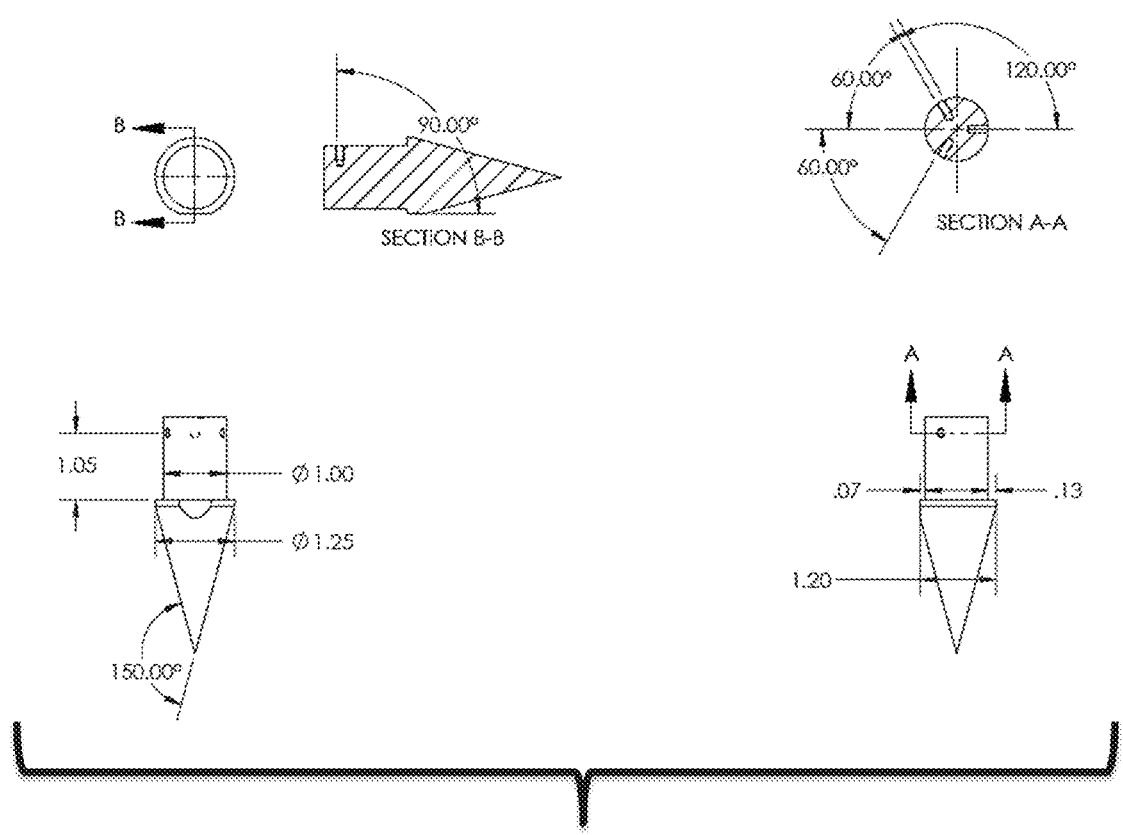
FIG. 16 shows a schematic view of a conical tip of a penetrometer according to an embodiment of the subject invention.

In many embodiments, the tip (e.g., conical tip) includes stainless steel and/or can be the first component of the penetrometer to be inserted into the soil sample. In some embodiments, the tip is hollow. In a specific embodiment, the diameter of the base of the (conical) tip measures approximately 1.25 inch, and the portion of the tip that connects with the tubular housing measures approximately 1.0 inch in diameter (FIG. 16). Advantageously, additional components and/or sensing devices can be attached to and/or enclosed in the tip with non-limiting examples including a capacitance sensor used for detecting degree of soil moisture.

In some embodiments, the connector (e.g., tubular connector) can enclose one or more sensing devices. Non-limiting examples of sensing devices include an auxiliary moisture sensor including electrodes that measure the electrical resistivity, and thus the moisture content, of the soil sample. In a particular embodiment, electrodes measuring resistivity can be attached to the wall of the connector and exposed to the surrounding soil sample. In many embodiments, the connector can be attached to the housing (e.g., tubular housing) at one end, preferably by welding, and detachably and securely connected to the extension rod at the opposite end. In a particular embodiment, the end of the connector that mates with the extension rod is machine-threaded.

Figure 17:
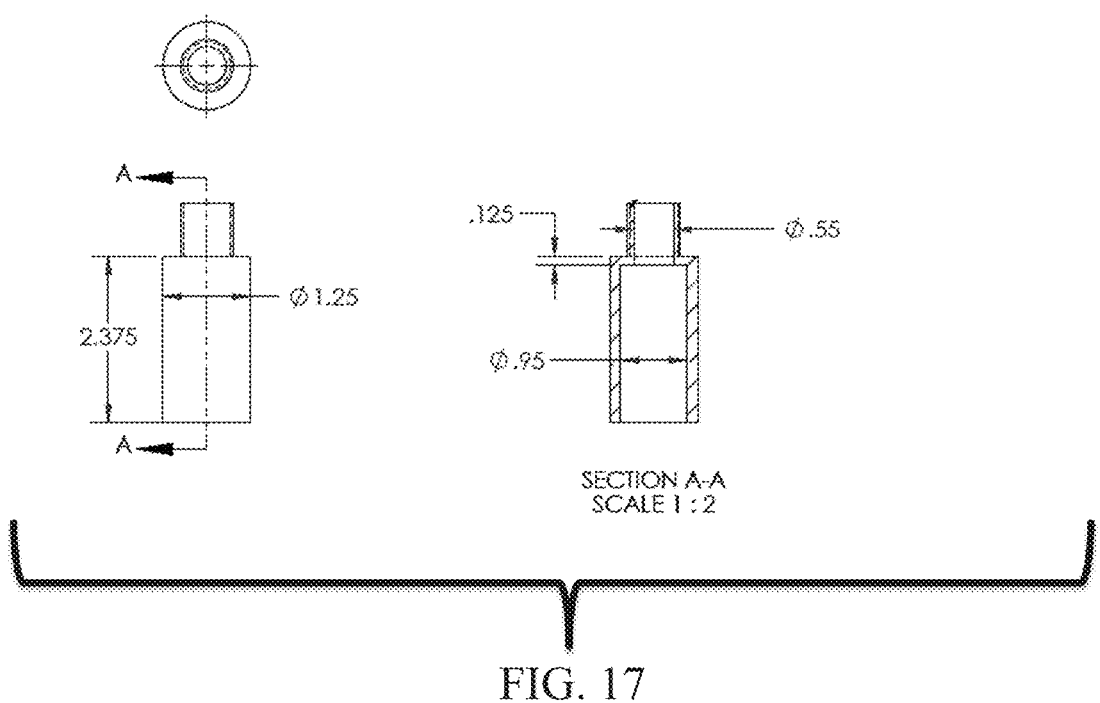
FIG. 17 shows a schematic view of a connector of a penetrometer according to an embodiment of the subject invention.

In an embodiment, the outer diameter of the connector measures approximately 1.25 inch, and the inner diameter measures approximately 0.95 inch. The threaded portion of the connector that mates with the extension rod can measure approximately 0.55 inch in diameter (FIG. 17).

In many embodiments, the extension rod (e.g., tubular extension rod) can be detachably connected to another device or a combination of devices at the end opposite to the connector. The ends of the extension rod can be threaded in order to facilitate easy removal of the penetrometer and other devices therefrom. In an embodiment, the extension rod can serve to attach the penetrometer to existing hydraulic soil sampling equipment that is optionally field-portable. In a further embodiment, a load cell can be threaded to the end of the extension rod opposite the penetrometer.

Figure 18:
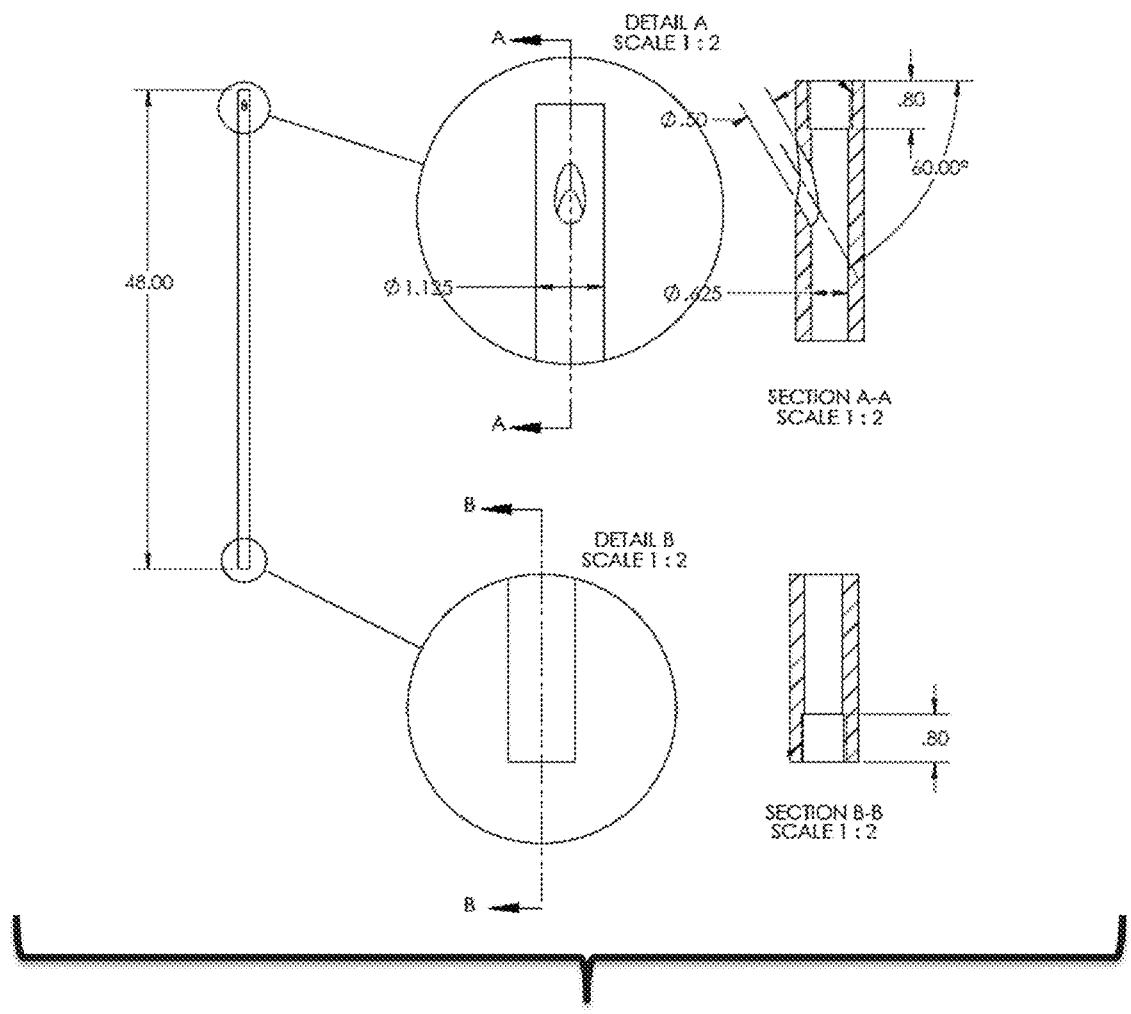
FIG. 18 shows a schematic view of an extension rod of a penetrometer according to an embodiment of the subject invention.

In an embodiment, the extension rod can measure approximately 1.125 inch in outer diameter and approximately 0.625 inch in inner diameter, and can be uniform in size throughout its length (FIG. 18).

The extension rod can include or be made of, for example, stainless steel, though embodiments are not limited thereto.

In many embodiments, a method of measuring soil reflectance can include using a soil Vis-NIR penetrometer as described herein for its intended purpose. In some embodiments, spectra can be collected at discrete depth intervals. During a discrete depth scan, the penetrometer is inserted into the soil to a specified depth at which a Vis-NIR spectrum is collected. In alternative embodiments, spectra can be collected continuously throughout the penetrometer's insertion. During continuous scans, the penetrometer is slowly inserted into the soil without stopping at any defined depth. Throughout the insertion, Vis-NIR spectra are collected as frequently as the instrumentation allows. In further embodiments, scans can be collected in intervals of approximately 2 to approximately 5 seconds (whether for continuous scan or during collection at discrete depth intervals).

The subject invention includes, but is not limited to, the following exemplified embodiments.

Embodiment 1. A soil penetrometer, comprising:
a conical tip capable of penetrating into a soil sample;
a tubular housing connected to the conical tip at one end;
a tubular connector attached to the tubular housing at one end; and
a tubular extension rod capable of being detachably connected to the connector at the end opposite to the tubular housing and detachably connected to another device or a combination of devices at the end opposite to the connector,
wherein the tubular housing comprises:
a transparent window built into the wall thereof, and
an optical module comprising a light-emitting device, a mirror capable of reflecting light (and/or configured to reflect light) generated by the light-emitting device, and a fiber optic sensor, wherein the sensor is positioned in the vicinity of the transparent window to receive signals reflected by the soil sample and transmit the signals to a spectrometer.

Embodiment 2. The penetrometer according to embodiment 1, wherein the connector encloses one or more sensing devices.

Embodiment 3. The penetrometer according to any of embodiments 1-2, comprising a moisture sensor enclosed in the connector.

Embodiment 4. The penetrometer according to any of embodiments 1-3, wherein the light-emitting device is a lamp.

Embodiment 5. The penetrometer according to any of embodiments 1-4, wherein the transparent window comprises sapphire.

Embodiment 6. The penetrometer according to any of embodiments 1-5, wherein the detecting end of the optic fiber is positioned with respect to the plane parallel to the transparent window at an angle between about 40 degrees and about 55 degrees that allows optimal spectral collection by the optic fiber.

Embodiment 7. The penetrometer according to any of embodiments 1-6, wherein the end of the optic fiber opposite to the detecting end extends through the connector and the extension rod and is connected to a Vis-NIR spectrometer.

Embodiment 8. The penetrometer according to any of embodiments 1-7, wherein the conical tip is hollow.

Embodiment 9. The penetrometer according to any of embodiments 1-8, capable of accommodating (or actually accommodates) a sensing device or a combination of devices (e.g., inside the tip, which may be hollow).

Embodiment 10. The penetrometer according to embodiments 9, wherein the sensing device is a capacitance sensor.

Embodiment 11. The penetrometer according to any of embodiments 1-10, wherein the optical module is enclosed in an aluminum housing (which may be the tubular housing or a second housing within the tubular housing).

Embodiment 12. The penetrometer according to any of embodiments 1-11, wherein the conical tip, the connector, and the extension rod each comprises stainless steel.

Embodiment 13. The penetrometer according to any of embodiments 1-12, wherein the end of the extension rod opposite to the connector is connected to a device selected from soil sampling equipment, soil coring equipment, a load cell, a displacement sensor, a time-domain reflectometer, and a combination thereof.

Embodiment 14. The penetrometer according to any of embodiments 1-13, wherein the optical fiber is configured in different geometries with respect to the plane parallel to the transparent window to obtain different signal-to-noise ratios.

Embodiment 15. The penetrometer according to any of embodiments 1-14, which is field-portable.

Embodiment 16. A method of measuring soil reflectance, comprising:
providing the soil penetrometer according to any of embodiments 1-15;
providing a soil sample; and
measuring the soil reflectance at a given depth within the sample using the soil penetrometer.

Embodiment 17. The method according to embodiment 16, wherein the soil reflectance is measured continuously as the penetrometer is inserted into the soil sample.

Embodiment 18. The method according to embodiment 16, wherein the soil reflectance is measured at discrete depths as the penetrometer is inserted into the soil sample.

Embodiment 19. A method of measuring soil reflectance, comprising:
providing a soil penetrometer, comprising:
a conical tip capable of penetrating into a soil sample, the tip comprising at least one sensing device;
a tubular housing connected to the conical tip at one end, comprising a transparent window built into the wall thereof and an optical module comprising a light-emitting device, a mirror capable of reflecting light (and/or configured to reflect light) generated by the light-emitting device, and a fiber optic sensor, wherein the sensor is positioned in the vicinity of the transparent window to receive signals reflected by the soil sample and transmits the signal to a Vis-NIR spectrometer;
a tubular connector attached to the tubular housing at one end, the connector comprising a built-in moisture sensor; and
a tubular extension rod capable of being detachably connected to the connector at the end opposite to the tubular housing and detachably connected to another device or a combination of devices selected from soil sampling equipment, soil coring equipment, a load cell, a displacement sensor, and a time-domain reflectometer, at the end opposite to the connector;

providing a soil sample; and measuring the soil reflectance at a given depth within the sample.

Embodiment 20. The method according to embodiment 19, wherein the soil reflectance is measured continuously as the penetrometer is inserted into the soil sample.

Embodiment 21. The method according to embodiment 19, wherein the soil reflectance is measured at discrete depths as the penetrometer is inserted into the soil sample.

Embodiment 22. A Vis-NIR soil penetrometer, comprising:

a conical tip capable of penetrating into a soil sample;

a tubular housing connected to the conical tip at one end;

a tubular connector attached to the tubular housing at one end, the connector comprising a built-in moisture sensor; and a tubular extension rod capable of being detachably connected to the connector at the end opposite to the tubular housing and detachably connected to another device or a combination of devices selected from soil sampling equipment, soil coring equipment, a load cell, a displacement sensor, and a time-domain reflectometer, at the end opposite to the connector, wherein the tubular housing comprises:

a transparent window built into the wall thereof; and an optical module comprising a light-emitting device, a mirror capable of reflecting light (and/or configured to reflect light) generated by the light-emitting device, and a fiber optic sensor, wherein the sensor is positioned in the vicinity of the transparent window to receive signals reflected by the soil sample and transmits the signal to a Vis-NIR spectrometer.

Embodiment 23. The penetrometer according to embodiment 22, which is field-portable.

A greater understanding of the present invention and of its many advantages may be had from the following examples, given by way of illustration. The following examples are illustrative of some of the methods, applications, embodiments and variants of the present invention. They are, of course, not to be considered as limiting the invention. Numerous changes and modifications can be made with respect to the invention.

EXAMPLE 1

Figures 5A, 5B:
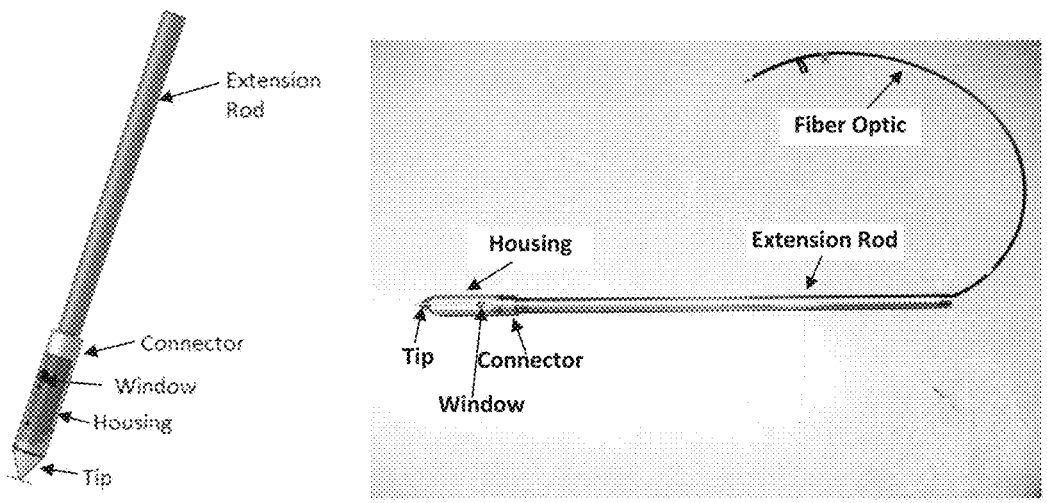
FIG. 5A shows a schematic of a penetrometer according to an embodiment of the subject invention.
FIG. 5B shows a schematic of a penetrometer according to an embodiment of the subject invention.
Figure 6A:
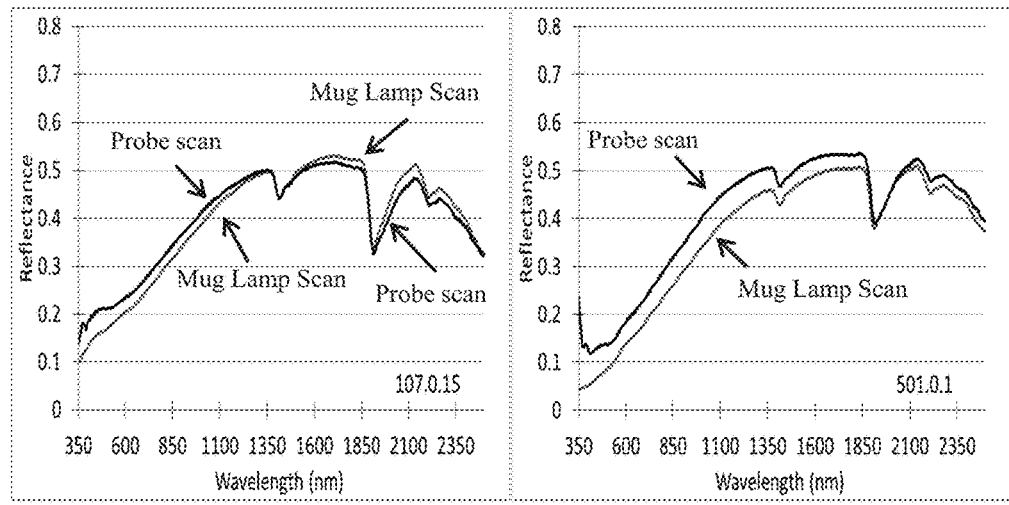
FIGS. 6A and 6B are soil scans acquired by a penetrometer according to an embodiment of the subject invention, in comparison with a standard mug lamp accessory. The scans are very close to each other for all four representative samples, indicating good performance of the penetrometer.
Figure 6B:
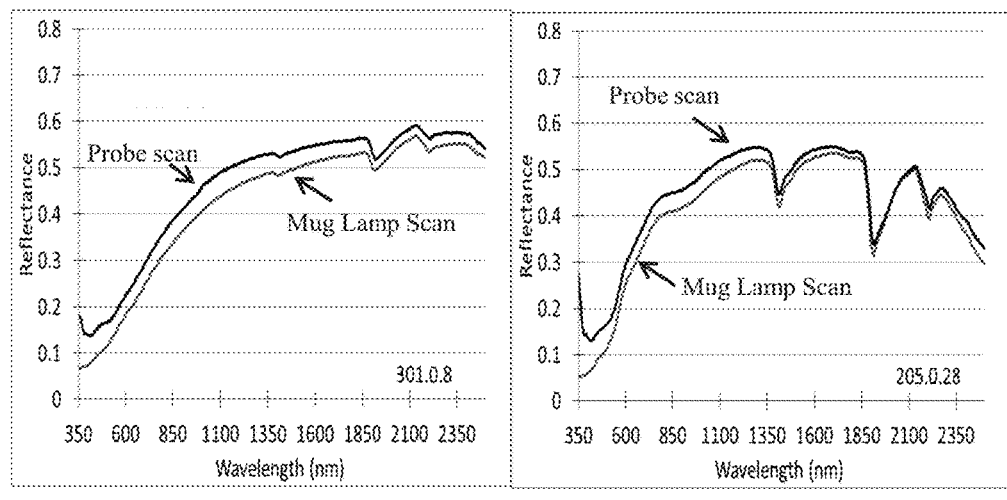
Figure 7A:
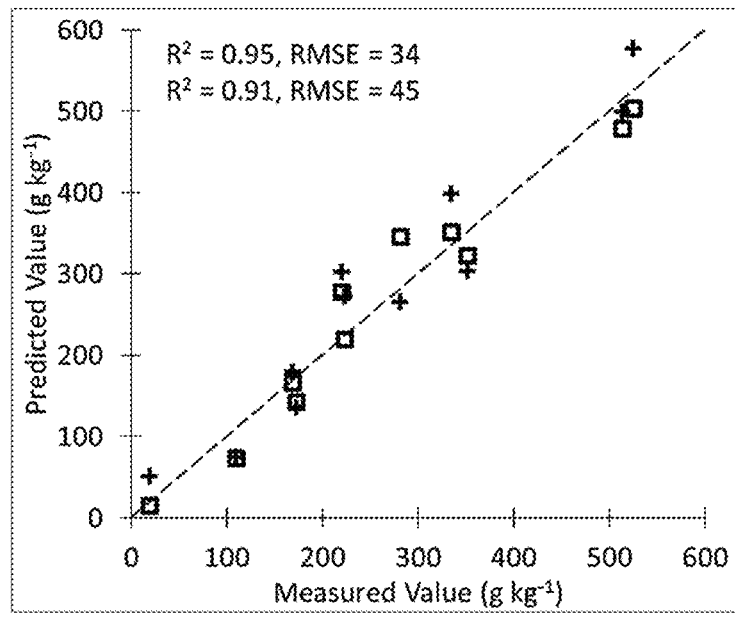
FIG. 7A shows clay Vis-NIR prediction results for selected samples. The model was calibrated by scans obtained with the mug lamp used for the data shown in FIGS. 6A and 6B.
Figure 7B:
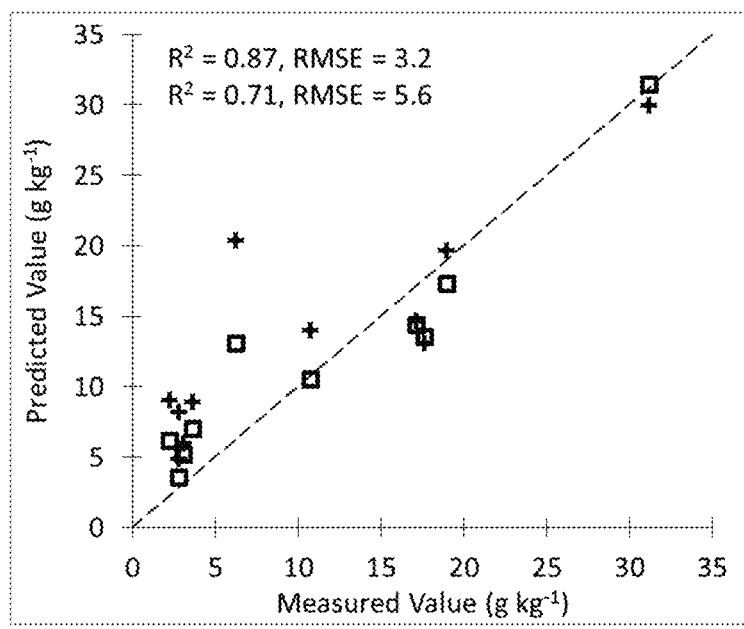
FIG. 7B shows organic carb Vis-NIR prediction results for selected samples. The model was calibrated by the scans obtained with the mug lamp used for the data shown in FIGS. 6A and 6B. For both FIGS. 7A and 7B, the squares are the scans acquired by the ASDi mug lamp, and the crosses are the scans by the penetrometer according to an embodiment of the subject invention.

To assess the functionality of a penetrometer of the subject invention (as shown in FIGS. 5A and 5B), spectral scans of four representative soil samples were analyzed and compared with the scans obtained using a standard mug lamp manufactured by Analytical Spectral Devices Inc. As shown in FIGS. 6A and 6B, the penetrometer demonstrated similar a spectral profile as the mug lamp, confirming its effectiveness in measuring soil reflectance. Further, measured Vis-NIR clay and organic carbon content in 11 selected samples were compared with predicted values using Travis Waiser's Central Texas dataset and demonstrated in FIGS. 7A and 7B.

EXAMPLE 2

Figure 10:
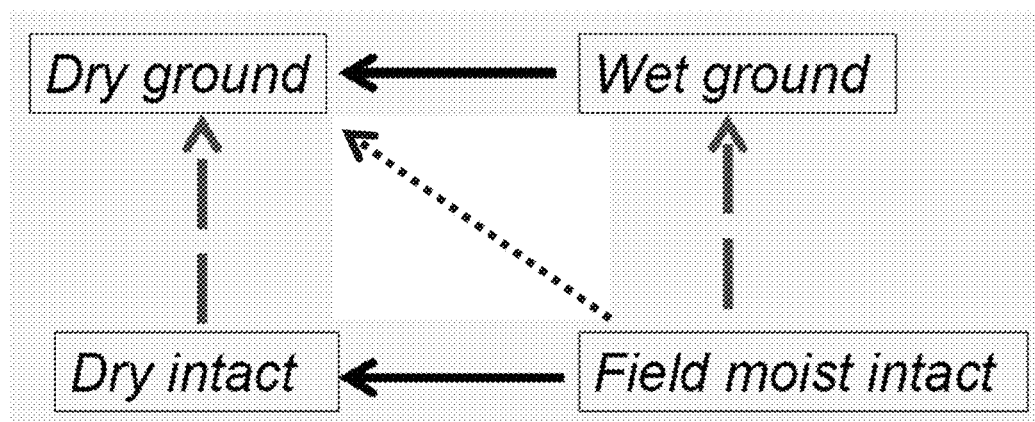
FIG. 10 is a schematic illustrating a Vis-NIR signal correction process.
Figure 13A:
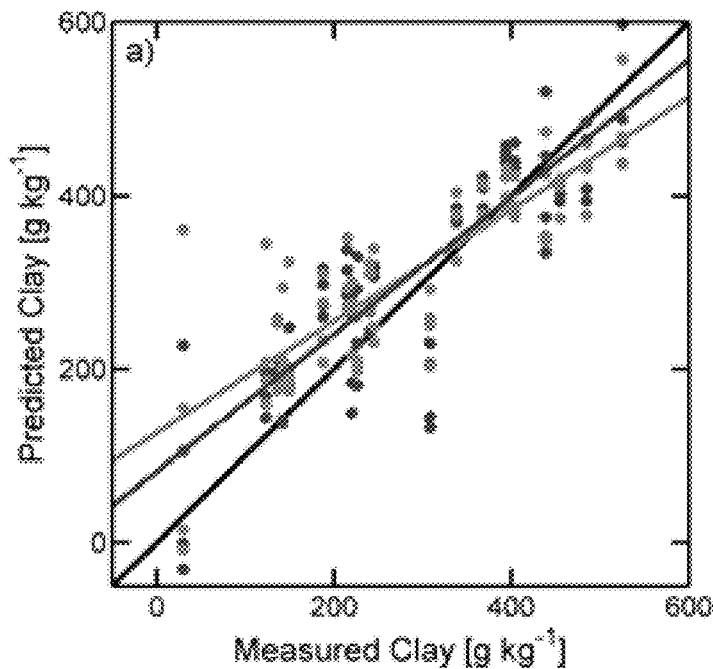
FIG. 13A shows predicted clay content for data projected with both the Texas and the Australia P-matrices of FIGS. 12A and 12B.
Figure 13B:
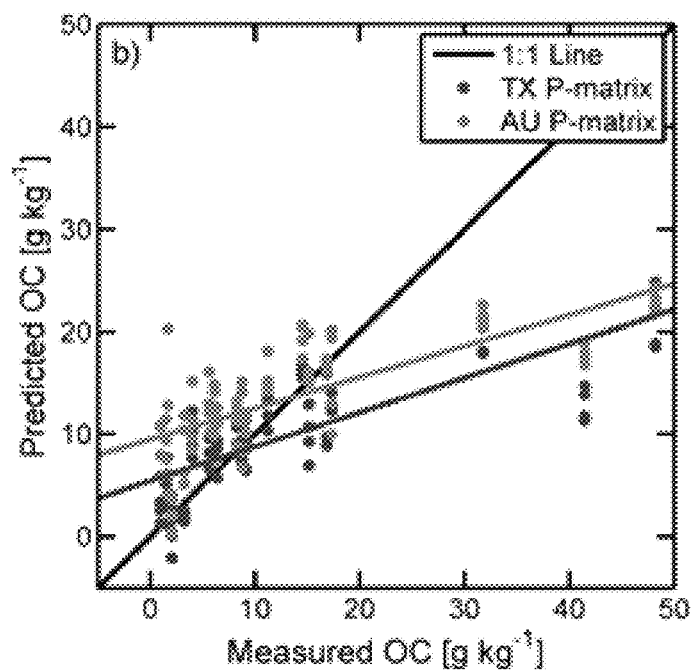
FIG. 13B shows the predicted organic carbon content for data projected with both the Texas and the Australia P-matrices of FIGS. 12A and 12B.

In situ Vis-NIR scans collected using a penetrometer disclosed herein can also be used to predict clay content of moist, intact soil samples using dry-ground sample spectral libraries with the help of a correction algorithm termed the external parameter orthogonalization (EPO). Due to the presence of water and soil heterogeneity, spectra collected in situ under moist conditions are distorted relative to the same soil sample collected in dry-ground state. It was found that EPO could remove these distortions multiplying intact spectra with a projection matrix, or P-matrix (FIG. 10). These results showed that the EPO can remove the effect of water content and soil heterogeneity from Vis-NIR spectra collected on intact soil cores. Applying EPO to Vis-NIR spectra collected using the penetrometer provided herein allows one to predict clay and organic carbon content of intact or in situ soil using dry ground spectral libraries for evaluation of soil properties in the field (FIG. 11).

The interchangeability of P-matrices developed on spectra from Texas and Australia was also tested (FIGS. 12A and 12B, respectively). The results showed that the two matrices were interchangeable providing strong evidence for the existence of a universal P-matrix, which could potentially allow the estimation of only one P-matrix for EPO correction using any spectral library.

Figure 8:
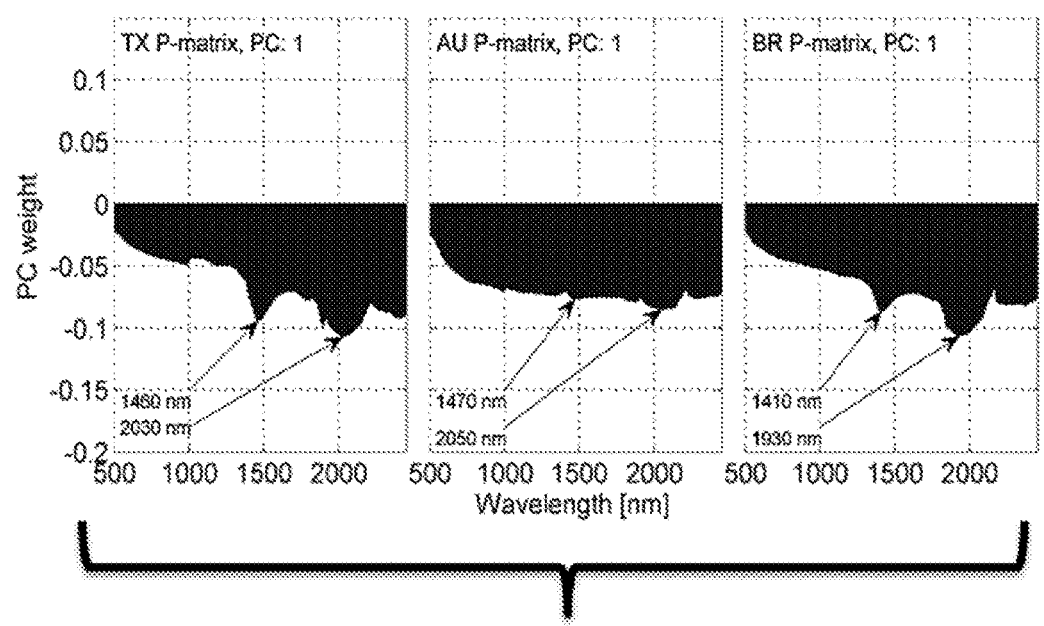
FIG. 8 shows the principal component loadings for the EPO for soils from Texas, Australia, and Brazil (left to right).

Testing of the EPO on soils from outside Texas was carried out and included tests of the EPO on Australian soils and Brazilian soils. Tests on Brazilian soils were conducted in conjunction with the University of São Paulo, Brazil. The results suggested that clay mineralogy affects the structure of the EPO transformation. Smectitic soils, (i.e., Texas and Australian soils), showed peaks in the EPO at approximately 2030 nm, whereas the kaolanitic samples from Brazil showed peaks at approximately 1930 nm (FIG. 8, where left to right are Texas, Australia, and Brazil as depicted in FIG. 8). These results suggest the EPO is transferable between soils of similar mineralogy but is not effective on soils of novel mineralogy.

It should be understood that the examples and embodiments described herein are for illustrative purposes only and that various modifications or changes in light thereof will be suggested to persons skilled in the art and are to be included within the spirit and purview of this application.

All patents, patent applications, provisional applications, and publications referred to or cited herein (including those in the "References" section) are incorporated by reference in their entirety, including all figures and tables, to the extent they are not inconsistent with the explicit teachings of this specification.

REFERENCES

Ben-Dor, E., Heller, D., Chudnovsky, A., 2008. A novel method of classifying soil profiles in the field using optical means. Soil Sci. Soc. Am. J. 72, 1113-1123.

Bogrekci, I., Lee, W. S., 2006. Effects of soil moisture content on absorbance spectra of sandy soils in sensing phosphorus concentrations using UV-VIS-NIR spectroscopy. Trans. ASABE 49, 1175-1180.

Bricklemyer, R. S., Brown, D. J., 2010. On-the-go VisNIR: potential and limitations for mapping soil clay and organic carbon. Comput. Electron. Agric. 70, 209-216.

Brown, D. J., Shepherd, K. D., Walsh, M. G., Mays, D. M., Reinsch, T. G., 2006. Global soil characterization with VisNIR diffuse reflectance library. Geoderma 132, 273-290.

Chang, C., Laird, D. L., Mausbach, M. J., Hurburgh, C. R., 2001. Near infrared spectroscopy—principal components regression analyses of soil properties. Soil Sci. Soc. Am. J. 65, 480-490.

Christy, C. D., 2008. Real-time measurement of soil attributes using on-the-go near infra-red reflectance spectroscopy. Comput. Electron. Agric. 61, 10-19.

Ge, Y., Morgan, C. L. S., Ackerson, J. P., 2014. VisNIR spectra of dried ground soils predict properties of soils scanned moist and intact. Geoderma 221-222, 61-69.

Gauch, H. G., Hwang, J. T. G., Fick, G. W., 2003. Model evaluation by comparison of model-based predictions and measured values. Agron. J. 95, 1442-1446.

Gee, G. W., Or, D., 2002. Particle-size analysis. In: Dane, J. H., Topp, G. C. (Eds.), Methods of Soil Analysis. Part 4. ASA, CSSA, and SSSA, Madison Wis., pp. 255-293.

Gomez, C., Viscarra Rossel, R., McBratney, A. B., 2008. Soil organic carbon prediction by hyperspectral remote sensing and field vis-NIR spectroscopy: an Australian case study. Geoderma 146, 103-411.

Idso, S. B., Jackson, R. D., Reginato, R. J., Kimball, B. A., Nakayama, F. S., 1975. Dependence of bare soil albedo on soil-water content. J. Appl. Meteorol. 14, 109-113.

Kaleita, A. L., Tian, L. F., Hirschi, M. C., 2005. Relationship between soil moisture content and soil surface reflectance. Trans. ASAE 48, 1979-1986.

Lobell, D. B., Asner, G. P., 2002. Moisture effects on soil reflectance. Soil Sci. Soc. Am. J. 66, 722-727.

Loeppert, R. H., Suarez, D. L., 1996. Carbonate and gypsum. In: Sparks, D. L. (Ed.), Methods of Soil Analysis. Part III. ASA, CSSA, and SSSA, Madison Wis.

Minasny, B., McBratney, A. B., Pichon, L., Sun, W., Short, M. G., 2009. Evaluating near infra-red spectroscopy for field prediction of soil properties. Aust. J. Soil Res. 4 664-673

Minasny, B., McBratney, A. B., Bellon-Maurel, V., Roger, J., Gobrecht, A., Ferrand, L., Joalland, S., 2011. Removing the effect of soil moisture from NIR diffuse reflectance spectra for the prediction of soil organic carbon. Geoderma 167-168, 118-124.

Morgan, C. L. S., Waiser, T. H., Brown, D. J., Hallmark, C. T., 2009. Simulated in situ character-ization of soil organic and inorganic carbon with visible near-infrared diffuse reflec-tance spectroscopy. Geoderma 151, 249-256.

Mouazen, A. M., Maleki, M. R., De Baerdemaeker, J., Ramon, H., 2007. On-line measurement of some selected soil properties using a VIS-NIR sensor. Soil Tillage Res. 93, 13-27.

Muller, E., Décamps, H., 2000. Modeling soil moisture-reflectance. Remote Sens. Environ. 76, 173-180.

Nelson, D. W., Sommers, L. E., 1996. Total C, organic C and organic matter. In: Sparks, D. L. (Ed.), Methods of Soil Analysis. Part III. ASA, CSSA, and SSSA, Madison Wis., pp. 961-1010.

Roger, J., Chauchard, F., Bellon-Maurel, V., 2003. EPO-PLS external parameter orthogonalization of PLS application to temperature-independent measurement of sugar content of intact fruits. Chemom. Intell. Lab. 66, 191-204.

Sankey, J. B., Brown, D. J., Bernard, M. L., Lawrence, R. L., 2008. Comparing local vs global visible and near-infrared (VisNIR) diffuse reflectance spectroscopy (DRS) calibrations for the prediction of soil clay, organic C and inorganic C. Geoderma 148, 149-158.

Shepherd, K. D., Walsh, M. G., 2002. Development of reflectance spectral libraries for characterization of soil properties. Soil Sci. Soc. Am. J. 66, 988-998.

Sherrod, L. A., Dunn, G., Peterson, G. A., Kolberg, R. L., 2002. Inorganic C analysis by modified pressure-calcimeter method. Soil Sci. Am. J. 66, 299-305.

Slaughter, D. C., Pelletier, M. G., Upadhyaya, S. K., 2001. Sensing soil moisture using NIR spectroscopy. Appl. Eng. Agric. 17, 241-247.

Stenberg, B., Viscarra Rossel, R. A., Mouazen, A. M., Wetterlind, J., 2010. Visible and near infrared spectroscopy in soil science. Adv. Agron. 107, 163-215.

Sudduth, K. A., Hummel, J. W., 1993. Portable, near infrared spectrometer for rapid soil analysis. Trans. ASAE 36, 185-193.

Twomey, S. A., Bohren, C. F., Mergenthaler, J. L., 1986. Reflectance and albedo differences between wet and dry surfaces. Appl. Optics 25, 431-437.

Viscarra Rossel, R. A., Walvoort, D. J. J., McBratney, A. B., Janik, L. J., Skjemstad, J. O., 2006. Visible, near infrared, mid infrared or combined diffuse reflectance spectroscopy for simultaneous assessment of various soil properties. Geoderma 131, 59-75.

Viscarra Rossel, R. A., Cattle, S. R., Ortega, A., Fouad, Y., 2009. In situ measurements of soil colour, mineral composition and clay content by vis-NIR spectroscopy. Geoderma 150, 253-266.

Waiser, T., Morgan, C. L. S., Brown, D. J., Hallmark, C. T., 2007. In situ characterization of soil clay content with visible near-infrared diffuse reflectance spectroscopy. Soil Sci. Soc. Am. J. 71, 389-396.

Zhu, Y., Weindorf, D. C., Chakraborty, S., Haggard, B., Johnson, S., Bakr, N., 2010. Character-izing surface soil water with field portable diffuse reflectance spectroscopy. J. Hydrol. 391, 135-142.

Ackerson, J. P., C. L. S Morgan, Y. Ge, A. B. McBratney, and B. Minasny. 2014. A universal transformation to remove the effect of water content from VisNIR. Paper presented at: 2013 Soil Survey & Land Resources Workshop, College Station, Tex.

Ackerson, J. P., C. L. S Morgan, Y. Ge, A. B. McBratney, and B. Minasny. 2013. Can orthogonal projections of VisNIR spectra yield useful information on soil water? Poster presented at: Water, Food, Energy, and Inovation for a Sustainable World. ASA, CSSA, and SSSA Annual Meetings, Tampa, Fla.

Ge, Y., C. L. S. Morgan, J. P. Ackerson. 2014. VISNIR spectra of dried ground soils predict properties of soils scanned moist and intact. Geoderma 221-222:61-69.

Poggio, M., Brown, D. J., Bricklemyer, R. S., 2015. Laboratory-based evaluation of optical performance for a new soil penetrometer visible and near-infrared (VisNIR) fore-optic. Comput. Electron. Agric. 115, 12-20.

Image from Veris Technologies e.g. Christy, 2008; Bricklemyer and Brown 2010 Waiser et al. 2007 (VisNIR for Proximal Sensing PPT slide)

Wilke, 2008 (Coefficient of Linear Extensibility PPT slide)

We claim:

1. A soil penetrometer, comprising:
a conical tip capable of penetrating into a soil sample;
a tubular housing connected to the conical tip at one end;
a tubular connector attached to the tubular housing at one end; and
a tubular extension rod capable of being detachably connected to the connector at the end opposite to the tubular housing and detachably connected to another device or a combination of devices at the end opposite to the connector,
wherein the tubular housing comprises:
a transparent window built into the wall thereof; and
an optical module comprising a light-emitting device, a mirror capable of reflecting light generated by the light-emitting device, and a fiber optic sensor, wherein the sensor is positioned in the vicinity of the transparent window to receive signals reflected by the soil sample and transmits the signal to a spectrometer, and wherein the conical tip is hollow.

2. The penetrometer according to claim 1, wherein the connector encloses one or more sensing devices.

3. The penetrometer according to claim 2, comprising a moisture sensor enclosed in the connector.

4. The penetrometer according to claim 1, wherein the light-emitting device is a lamp.

5. The penetrometer according to claim 1, wherein the transparent window comprises sapphire.

6. The penetrometer according to claim 1, wherein the detecting end of the optic fiber is positioned with respect to the plane parallel to the transparent window at an angle between about 40 degrees and about 55 degrees that allows optimal spectral collection by the optic fiber.

7. The penetrometer according to claim 6, wherein the end of the optic fiber opposite to the detecting end extends through the connector and the extension rod and is connected to a Vis-NIR spectrometer.

8. The penetrometer according to claim 1, wherein the hollow conical tip accommodates a sensing device or a combination of devices therein.

9. The penetrometer according to claim 8, wherein the sensing device is a capacitance sensor.

10. The penetrometer according to claim 1, wherein the optical module is enclosed in the tubular housing, and the tubular housing comprises aluminum.

11. The penetrometer according to claim 1, wherein the conical tip, the tubular housing, the connector, and the extension rod each comprises stainless steel.

12. The penetrometer according to claim 1, wherein the end of the extension rod opposite to the connector is connected to a device selected from soil sampling equipment, soil coring equipment, a load cell, a displacement sensor, a time-domain reflectometer, and a combination thereof.

13. The penetrometer according to claim 1, wherein the optical fiber is configured in different geometries with respect to the plane parallel to the transparent window to obtain different signal-to-noise ratios.

14. The penetrometer according to claim 1, which is field-portable.

15. A method of measuring soil reflectance, comprising:
providing a soil penetrometer, comprising:
a conical tip capable of penetrating into a soil sample, the tip comprising at least one sensing device;
a tubular housing connected to the conical tip at one end;
a tubular connector attached to the tubular housing at one end, the connector comprising a built-in moisture sensor; and
a tubular extension rod capable of being detachably connected to the connector at the end opposite to the tubular housing and detachably connected to another device or a combination of devices selected from soil sampling equipment, soil coring equipment, a load cell, a displacement sensor, and a time-domain reflectometer, at the end opposite to the connector,
wherein the tubular housing comprises:
a transparent window built into the wall thereof; and
an optical module comprising a light-emitting device, a mirror capable of reflecting light generated by the light-emitting device, and a fiber optic sensor, wherein the sensor is positioned in the vicinity of the transparent window to receive signals reflected by the soil sample and transmits the signal to a Vis-NIR spectrometer;
providing a soil sample; and
measuring the soil reflectance at a given depth within the sample,
wherein the soil reflectance is measured continuously as the penetrometer is inserted into the soil sample.

* * * * *